US008836939B2

(12) United States Patent
Gono (10) Patent No.: US 8,836,939 B2
(45) Date of Patent: Sep. 16, 2014

(54) PROBE AND OPTICAL MEASUREMENT APPARATUS

(75) Inventor: Kazuhiro Gono, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/482,730

(22) Filed: May 29, 2012

(65) Prior Publication Data

US 2013/0016347 A1 Jan. 17, 2013

Related U.S. Application Data

(63) Continuation of application No. PCT/JP2011/074565, filed on Oct. 25, 2011.

(60) Provisional application No. 61/408,192, filed on Oct. 29, 2010.

(51) Int. Cl.
*G01J 1/02* (2006.01)
*A61B 1/12* (2006.01)
*A61B 1/00* (2006.01)

(52) U.S. Cl.
CPC ........... *A61B 1/0017* (2013.01); *A61B 1/00057* (2013.01); *A61B 1/12* (2013.01)
USPC ............ 356/243.1; 356/477; 606/13; 606/16; 606/17; 607/92; 600/480

(58) Field of Classification Search
CPC ..... A61B 18/14; G01B 9/0205; G02B 6/3604
USPC .................. 356/243.1, 477; 606/13; 607/922; 600/480
See application file for complete search history.

(56) References Cited

U.S. PATENT DOCUMENTS 5,902,246 A 5/1999 McHenry et al.
2005/0288654 A1* 12/2005 Nieman et al. .................. 606/13

(Continued)

FOREIGN PATENT DOCUMENTS

CN 101548153 A 9/2009
JP A-2000-507858 6/2000

(Continued)

OTHER PUBLICATIONS

Jun. 19, 2012 Decision of a Patent Grant issued in Japanese Patent Application No. 2012-523541 (with English Translation).

(Continued)

*Primary Examiner* — Baisakhi Roy
(74) *Attorney, Agent, or Firm* — Oliff PLC (57) ABSTRACT

A probe detachably connected to an optical measurement apparatus includes: a fiber that emits light by the optical measurement apparatus, and outputs reflected light and/or scattered light from an object to be measured; a covering member that covers a side face of the fiber; a cap that covers a distal end of the probe; a standard object that is provided on a surface of the cap facing the distal end of the fiber and that is used in calibration measurement by light emitted from the distal end of the fiber; an adhesive member that adheres the cap to the distal end of the probe and is made of an adhesive material; a heat-generating portion that generates heat to be applied to the adhesive member; and a thermal conduction portion that conducts heat that decreases the adhesive strength of the adhesive material with respect to the covering member.

22 Claims, 11 Drawing Sheets

(56) References Cited

U.S. PATENT DOCUMENTS

2008/0037024 A1    2/2008  Backman et al.
2009/0244545 A1*  10/2009  Toida ............................ 356/477
2011/0196457 A1*  8/2011  Irwin .............................. 607/92

FOREIGN PATENT DOCUMENTS

JP      A-2009-537014    10/2009
WO    WO 2007/133684 A2   11/2007

OTHER PUBLICATIONS

Jan. 10, 2012 International Search Report issued in PCT/JP2011/074565.

Aug. 7, 2013 Supplementary European Search Report issued in EP 11836281.3.

May 6, 2014 Office Action issued in Chinese Patent Application No. 201180010811.4.

* cited by examiner

PROBE AND OPTICAL MEASUREMENT APPARATUS

CROSS-REFERENCE TO RELATED APPLICATIONS

This application is a continuation of PCT international application Ser. No. PCT/JP2011/074565 designating the United States and filed on Oct. 25, 2011 which claims the benefit of priority from U.S. provisional patent application No. 61/408,192, filed on Oct. 29, 2010, and the entire contents of the PCT international application and the U.S. provisional patent application are incorporated herein by reference.

BACKGROUND OF THE INVENTION

1. Field of the Invention

The present invention relates to an in-vivo insertable probe to be detachably connected to an optical measurement apparatus, and an optical measurement apparatus to which the probe is connected.

2. Description of the Related Art

In recent years, an optical measurement apparatus has been proposed, which irradiates a biological tissue with incoherent light from a distal end of a probe and measures scattered light from the biological tissue to detect characteristics of the biological tissue (see, for example, for example, International Patent Publication Pamphlet No. WO 2007/133684). Such an optical measurement apparatus performs optical measurement in combination with an endoscope that observes internal organs such as digestive organs.

SUMMARY OF THE INVENTION

A probe according to an aspect of the present invention is a probe detachably connected to an optical measurement apparatus and includes: a fiber that emits, from a distal end thereof, light supplied from a proximal end thereof by the optical measurement apparatus, and outputs, from the proximal end to the optical measurement apparatus, reflected light and/or scattered light from an object to be measured, the reflected light and/or scattered light entering from the distal end; a covering member that covers a side face of the fiber; a cap that covers a distal end of the probe; a standard object that is provided on a surface of the cap facing the distal end of the fiber and that is used in calibration measurement by light emitted from the distal end of the fiber; an adhesive member that adheres the cap to the distal end of the probe and is made of an adhesive having an adhesive strength with respect to the covering member, the adhesive strength decreasing by application of heat; a heat-generating portion that generates heat to be applied to the adhesive member; and a thermal conduction portion that conducts, to the covering member, the heat that decreases the adhesive strength of the adhesive material with respect to the covering member.

An optical measurement apparatus according to another aspect of the present invention includes: a probe including: a fiber that emits, from a distal end thereof, light supplied from a proximal end thereof by the optical measurement apparatus, and outputs, from the proximal end to the optical measurement apparatus, reflected light and/or scattered light from an object to be measured, the reflected light and/or scattered light entering from the distal end; a covering member that covers a side face of the fiber; a cap that covers a distal end of the probe; a standard object that is provided on a surface of the cap facing the distal end of the fiber and that is used in calibration measurement by light emitted from the distal end of the fiber; an adhesive member that adheres the cap to the distal end of the probe and is made of an adhesive having an adhesive strength with respect to the covering member, the adhesive strength decreasing by application of heat; a heat-generating portion that generates heat to be applied to the adhesive member; and a thermal conduction portion that conducts, to the covering member, the heat that decreases the adhesive strength of the adhesive material with respect to the covering member; a connector to which a proximal end of the probe is detachably connected; a light source that supplies light to the probe via the connector; a light-receiving unit that receives via the connector light output from the probe; a measurement unit that measures a characteristic of the object to be measured based on a result of the light-reception by the light-receiving unit; and a calibration processing unit that performs a calibration process of the optical measurement apparatus and the probe.

The above and other features, advantages, and technical and industrial significance of the present invention will be better understood by reading the following detailed description of the present invention when considered in connection with the accompanying drawings.

DETAILED DESCRIPTION OF THE PREFERRED EMBODIMENTS

Hereinafter, preferred embodiments of a probe and an optical measurement apparatus according to the present invention will be described in detail with reference to the drawings. The invention is not limited by the embodiments. In the description of drawings, like reference numerals denote like elements. Further, it is to be noted that the drawings are schematic, and relations between thicknesses and widths of each element, and ratios among elements are different from those of the actual. Among the drawings also, a same portion having relations or ratios of dimensions different from one another is included.

First Embodiment

Figure 1:
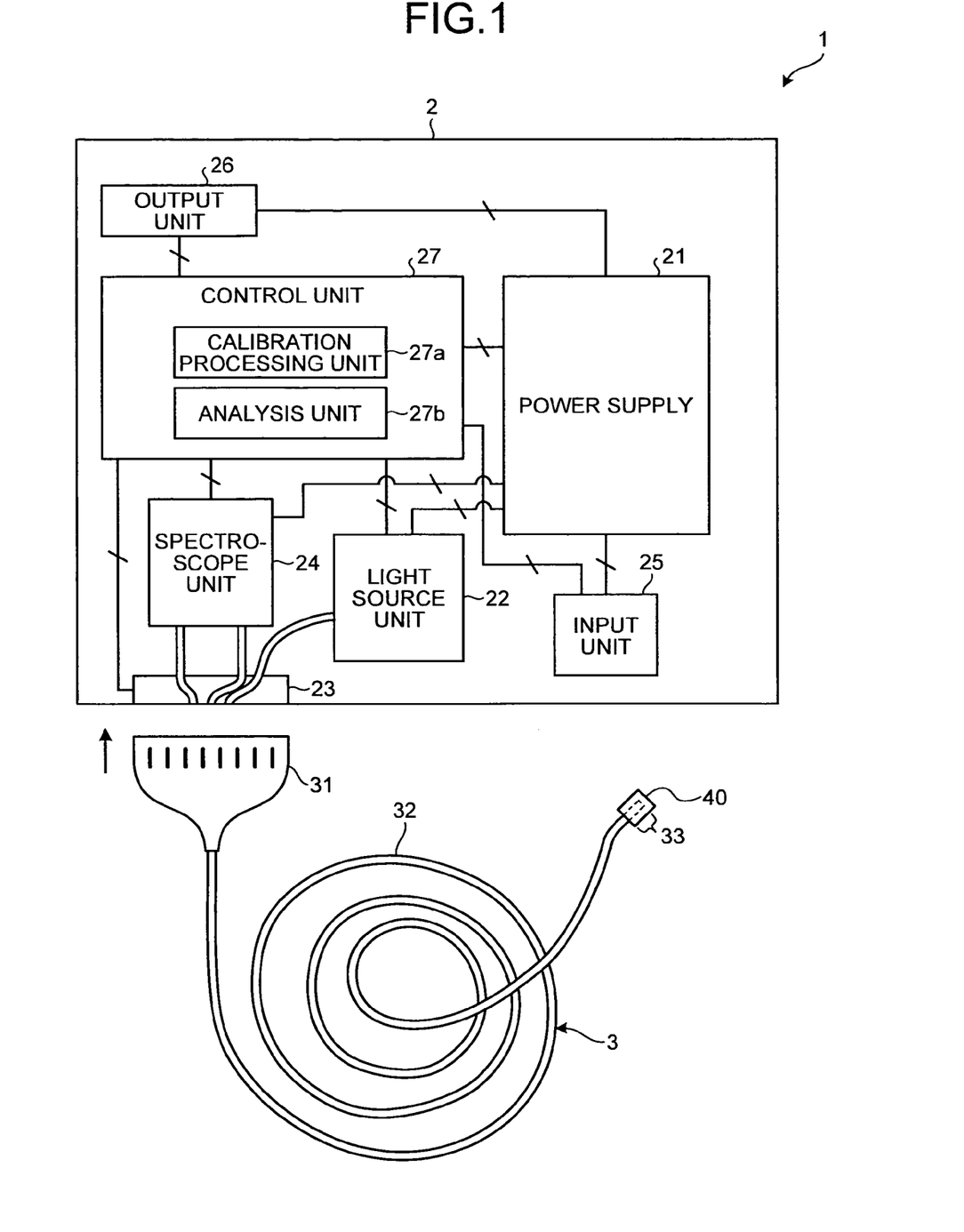
FIG. 1 is a schematic diagram illustrating a schematic configuration of an optical measurement apparatus according to a first embodiment.

FIG. 1 is a schematic diagram illustrating a schematic configuration of an optical measurement apparatus according to a first embodiment of the present invention. As illustrated in FIG. 1, an optical measurement apparatus 1 according to the first embodiment includes a detection device 2 that performs optical measurement with respect to an object to be measured such as a biological tissue and detects characteristic of the object to be measured, and a probe 3 to be inserted into a subject. The probe 3 emits from a distal end thereof light supplied from a proximal end thereof to the object to be measured and outputs from the proximal end scattered light from the object to be measured, the scattered light entering from the distal end, to the detection device 2.

The detection device 2 includes a power supply 21, a light source unit 22, a connector 23, a spectroscope unit 24, an input unit 25, an output unit 26, and a control unit 27.

The power supply 21 supplies power to each element of the detection device 2.

The light source unit 22 emits light to irradiate the object to be measured. The light source unit 22 is implemented using a light source such as a white light-emitting diode (LED), a xenon lamp, or laser, and one lens or a plurality of lenses as necessary. The light source unit 22 supplies light to be irradiated onto the object to be measured to the probe 3 via the connector 23. The light source unit 22 has, for example, an incoherent light source as the light source.

The connector 23 is detachably connected to the probe 3. The connector 23 detachably connects the proximal end of the probe 3 to the detection device 2. The connector 23 supplies the light emitted by the light source unit 22 to the probe 3 and outputs, to the spectroscope unit 24, the scattered light output from the probe 3. The connector 23 outputs, to the control unit 27, information on whether the probe 3 has been connected.

The spectroscope unit 24 receives detected light, which is the scattered light from the object to be measured and is the light output from the probe 3. The spectroscope unit 24 is implemented using a spectroscope. The spectroscope unit 24 receives the scattered light output from the probe 3 via the connector 23 and measures a spectral component and an intensity of the received scattered light. The spectroscope unit 24 outputs a result of the measurement to the control unit 27.

The input unit 25 is implemented using a push-type switch or the like and receives instruction information for instructing activation of the detection device 2 and various other types of instruction information and inputs them to the control unit 27 by manipulation of a switch or the like.

The output unit 26 outputs information related to various processes in the optical measurement apparatus 1. The output unit 26 is implemented using a display, a speaker, a motor, or the like and outputs information related to various processes in the optical measurement apparatus 1 by outputting image information, audio information, or vibration.

The control unit 27 controls processing operations of each element of the detection device 2. The control unit 27 is implemented using a central processing unit (CPU) and a semiconductor memory such as a random access memory (RAM). The control unit 27 controls operations of the detection device 2 by transferring and the like instruction information and data to respective elements of the detection device 2. The control unit 27 includes a calibration processing unit 27a and an analysis unit 27b.

The calibration processing unit 27a controls the light source unit 22 and the spectroscope unit 24, and before starting detection with respect to the object to be measured, performs a calibration process with respect to the detection device 2 and the probe 3 to guarantee detection accuracy. In this calibration process, the calibration processing unit 27a irradiates a white plate having stable reflection characteristics with light as in an actual measurement. Based on a result of the measurement in the spectroscope unit 24 of the scattered light from the white plate, the calibration processing unit 27a performs a calibration process of calibrating a white balance that becomes a reference. The analysis unit 27b analyzes characteristics of the object to be measured based on the result of the measurement by the spectroscope unit 24.

The probe 3 is implemented using an optical fiber or a plurality of optical fibers. For example, the probe 3 includes an irradiation fiber that irradiates the object to be measured with the light supplied from the light source and a light-collecting fiber into which the scattered light from the object to be measured enters. When a low-coherence enhanced backscattering (LEBS) technique is used, a plurality of light-collecting fibers are provided to collect each of at least two scattered light beams having different scattering angles. The probe 3 includes a proximal end portion 31 detachably connected to the connector 23 of the detection device 2, a flexible portion 32 having flexibility, and a distal end portion 33 from which the light supplied from the light source unit 22 is emitted and into which the scattered light from the object to be measured enters.

Figure 2:
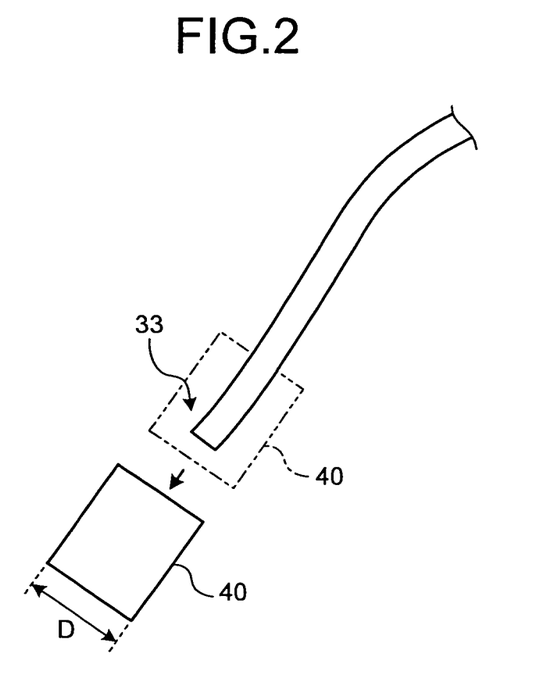
FIG. 2 is a diagram for explaining a distal end portion of a probe in FIG. 1.
Figure 3:
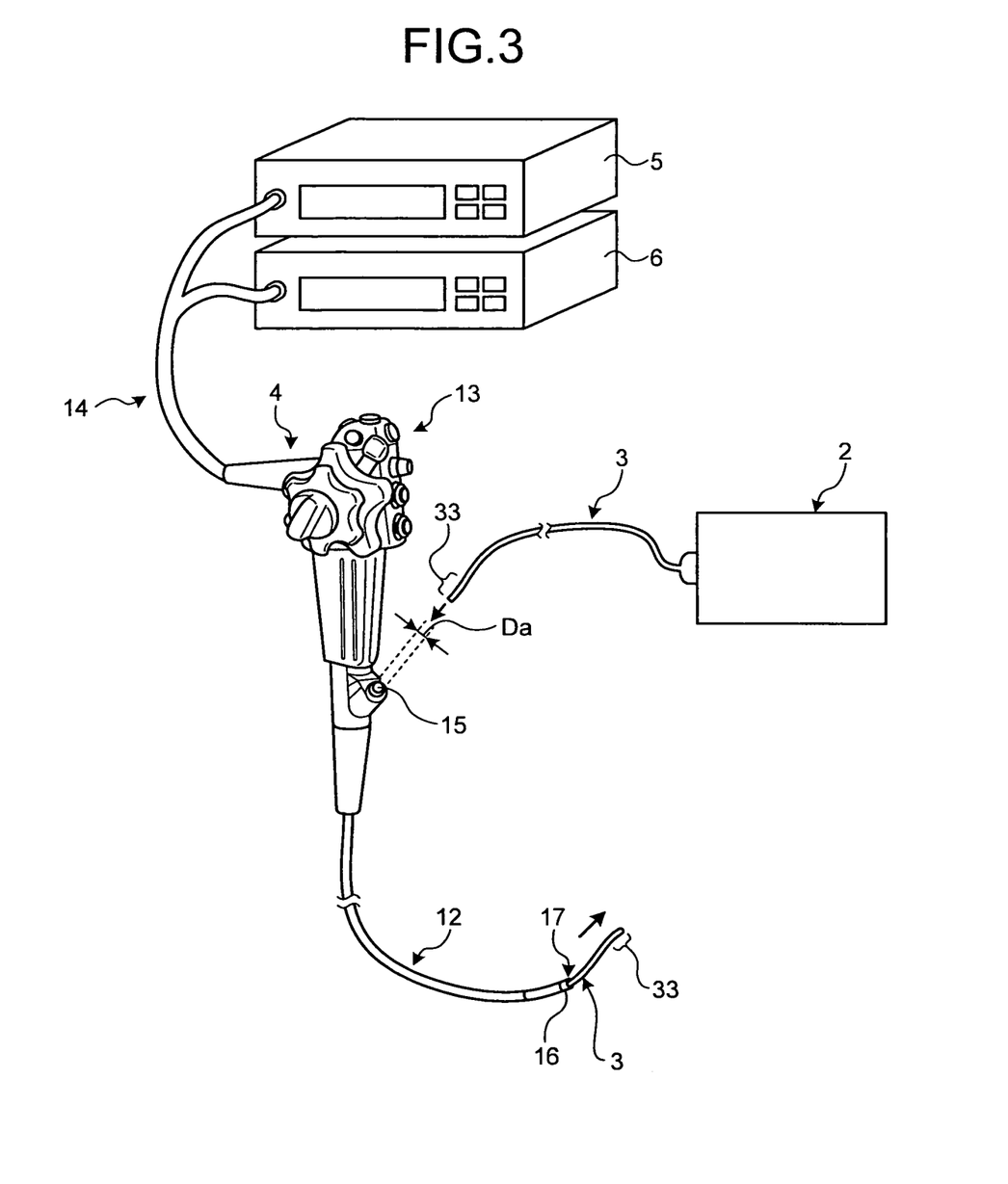
FIG. 3 is a diagram illustrating a configuration of an examination system and installation of the probe.

The probe 3 is provided with a cap 40 being installed, the cap 40 covering the distal end portion 33. When examination using the probe 3 is performed, the probe 3 is used with the cap 40 being removed from the distal end portion 33 of the probe 3 as illustrated in FIG. 2. FIG. 3 is a diagram illustrating a configuration of an examination system and installation of the probe 3. In FIG. 3, a flexible universal cord 14 extending from a side portion of a manipulation unit 13 is connected to a light source device 5 and to a signal processing device 6 that processes a subject image captured at a distal end portion 16 of an endoscope 4. The probe 3 is inserted from a probe channel insertion hole 15 in the vicinity of the manipulation unit 13 of an out-of-body portion of the endoscope 4 inserted into the subject. The distal end portion 33 of the probe 3 passes through the inside of an insertion portion 12 and protrudes from an aperture 17 of the distal end portion 16 connected to a probe channel. As a result, the probe 3 is inserted inside the subject, and optical measurement is started.

In the optical measurement apparatus 1, an outer diameter D of the cap 40 (see FIG. 2) is set to be larger than a diameter Da of the probe channel insertion hole 15. Therefore, when the cap 40 stays fitted on the distal end portion 33 of the probe 3, the distal end portion 33 of the probe 3 is not insertable into the probe channel insertion hole 15 and the measurement process is unable to be started.

Figure 4:
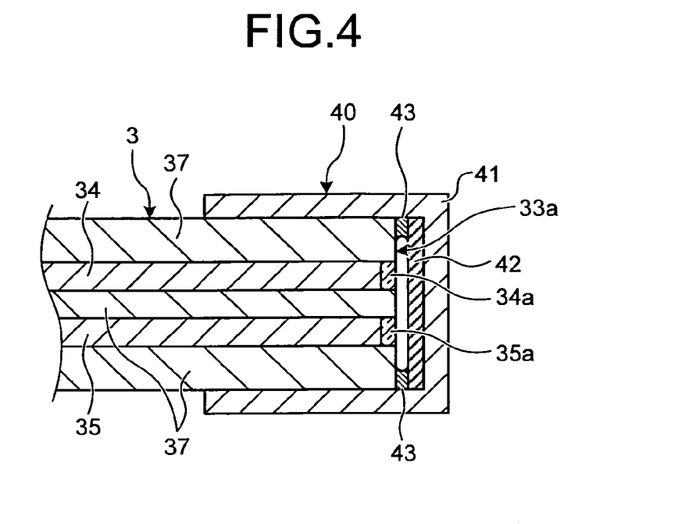
FIG. 4 is a cross-sectional view illustrating a distal end portion of the probe illustrated in FIG. 1 cut along an axial direction of the probe.

Next, the distal end portion 33 of the probe 3 illustrated in FIG. 1 and the cap 40 that covers the distal end portion 33 will be described. FIG. 4 is a cross-sectional view illustrating the distal end portion 33 of the probe 3 illustrated in FIG. 1 cut along an axial direction of the probe 3.

As illustrated in FIG. 4, the probe 3 has, inside thereof, an irradiation fiber 34 extending from the proximal end portion 31 to the distal end portion 33 of the probe 3 and a light-collecting fiber 35 extending from the proximal end portion 31 to the distal end portion 33 of the probe 3. A covering member 37 covers side faces of the irradiation fiber 34 and the light-collecting fiber 35. The irradiation fiber 34 emits, by the detection device 2, the light supplied from the proximal end (not illustrated) of the irradiation fiber 34 from the distal end of the irradiation fiber 34 to the outside via an irradiation lens 34a at the distal end. The light-collecting fiber 35 outputs, from the proximal end (not illustrated) of the light-collecting fiber 35 to the detection device 2 via a light-collecting lens 35a of the distal end, the light that has entered from the distal end of the light-collecting fiber 35.

The cap 40 has a cap body 41 having an inner diameter and an internal shape corresponding to an outer diameter and a shape of the distal end portion 33. The cap 40 is provided with a white plate 42. The white plate 42 is provided on an inner surface of the cap 40 facing the distal end of the irradiation fiber 34 and is used in the calibration measurement with the light emitted from the distal end of the irradiation fiber 34. The white plate 42 is formed of a material having a thermal conductivity.

An inner portion of the cap 40 and the distal end portion 33 of the probe 3 are adhered to each other using an adhesive 43 (adhesive member). The adhesive 43 adheres the inner portion of the cap 40 to a distal end face 33a of the distal end portion 33 of the probe 3. A position of the adhesive 43 is set to a position not influencing detection.

This adhesive 43 is a thermoplastic adhesive that melts when heat is applied. The adhesive 43 has an adhesive strength with respect to the covering member 37 that decreases by heat and the adhesive 43 has a property that the adhesive strength to the cap 40 becomes stronger than the adhesive strength to the covering member 37 when heat is applied. In a light-irradiated portion of the white plate 42, heat is generated by being irradiated with light, and the adhesive 43 is melted by conduction of the generated heat from the white plate 42 to the adhesive 43. The adhesive 43 is melted by the heat generated based on the light supplied by the light source unit 22 during an interval between start to end of the calibration process, by adjustment of an adhesive amount, an adhesive area, or the like. Since the adhesive 43 melts when the calibration process is finished, the cap 40 becomes removable from the distal end portion 33 of the probe 3 after the calibration process is finished.

Figure 5:
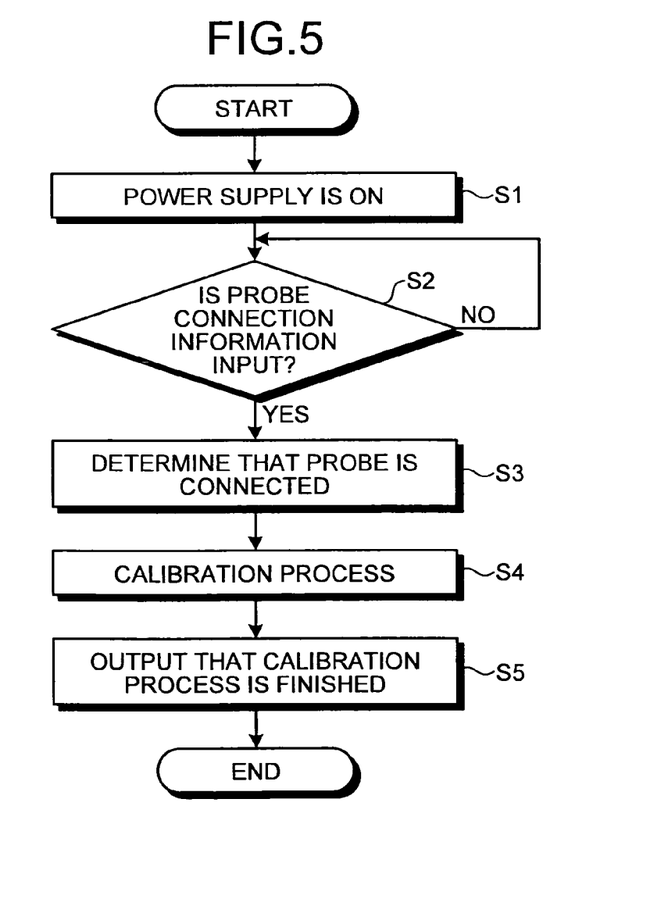
FIG. 5 is a flowchart illustrating a processing sequence until the optical measurement apparatus illustrated in FIG. 1 finishes a calibration process.

Next, a processing sequence in the optical measurement apparatus 1 until the calibration process is finished will be described. FIG. 5 is a flowchart illustrating a processing sequence in the optical measurement apparatus 1 illustrated FIG. 1 until the calibration process is finished.

As illustrated in the flowchart of FIG. 5, the power supply 21 is turned on by manipulation of a predetermined switch in the input unit 25 (step S1). The control unit 27 determines whether probe connection information indicating connection of the probe 3 to the detection device 2 has been input from the connector 23 (step S2). When the control unit 27 determines that the probe connection information has not been input (NO in step S2), the control unit 27 repeats the determination process in step S2 until the control unit 27 determines that the probe connection information has been input.

When the control unit 27 determines that the probe connection information has been input (YES in step S2), the control unit 27 determines that the probe 3 has been connected to the detection device 2 (step S3) and the calibration processing unit 27a performs the calibration process (step S4).

After the calibration process in step S4 is finished, the control unit 27 causes the output unit 26 to output that the calibration process is finished (.step S5) and finishes the calibration process.

Figure 6:
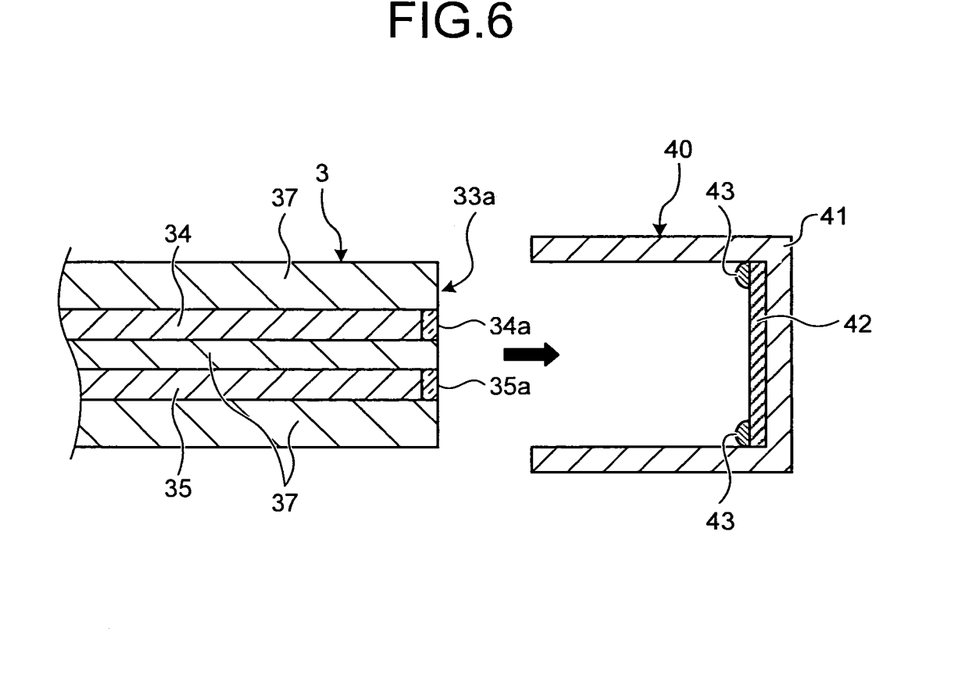
FIG. 6 is a cross-sectional view for explaining removal of a cap from the distal end portion of the probe illustrated in FIG. 1.

Here, the adhesive 43 used to adhere the cap 40 to the distal end portion 33 of the probe 3 is melted by the heat generated based on the light supplied by the light source unit 22 during the interval between the start and the end of the calibration process. Therefore, when the calibration process is finished, the cap 40 becomes separable from the distal end portion 33 of the probe 3, and removable from the distal end portion 33 of the probe 3 as illustrated in FIG. 6. The distal end portion 33 of the probe 3 with the cap 40 removed is insertable into the probe channel insertion hole 15 of the endoscope 4, and measurement on an actual object to be measured is able to be started. In addition, the adhesive 43 has a property that the adhesive strength to the cap 40 becomes stronger than the adhesive strength to the distal end portion 33 of the probe 3 when heat is applied. Therefore, when the cap 40 is removed from the probe 3, the adhesive 43 adheres to the cap 40 side as illustrated in FIG. 6, and does not remain on the distal end portion 33 of the probe 3.

As described, in the first embodiment, when the power supply of the detection device 2 is turned on, and the probe 3 is connected to the detection device 2, the calibration process is automatically performed, and after the calibration process is finished, the cap becomes removable for the first time. Accordingly, in the first embodiment, it is possible to infallibly perform the calibration process before measurement on an actual object to be measured, and to obtain a proper measurement result.

Figure 7:
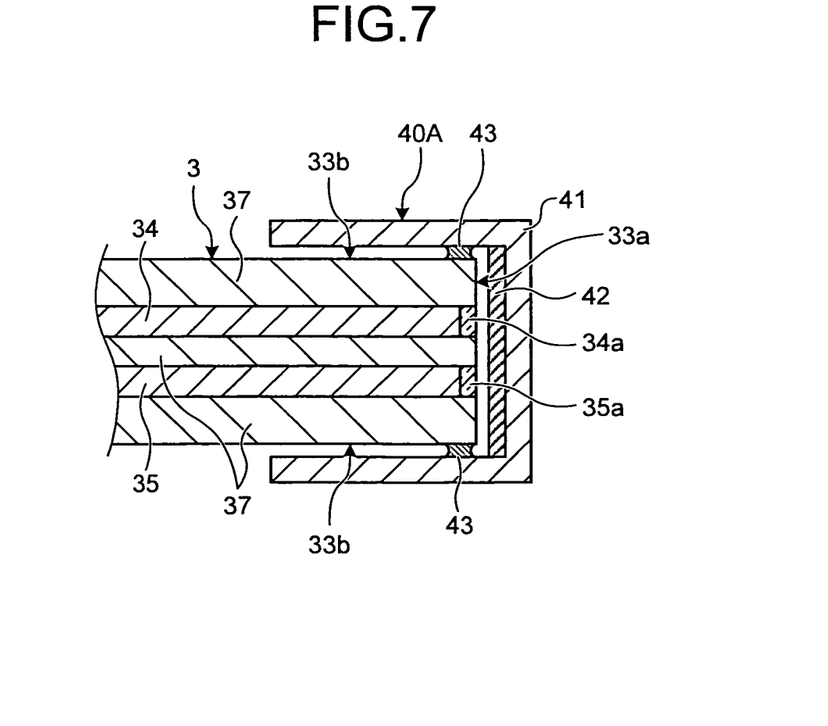
FIG. 7 is a cross-sectional view illustrating another example of the distal end portion of the probe illustrated in FIG. 1.

Although description has been made for a case where the adhesive 43 adheres the inner portion of the cap 40 to the distal end face 33a of the distal end portion 33 of the probe 3 in the first embodiment, the adhesive 43 is not limited thereto. For example, as illustrated in FIG. 7, the adhesive 43 may adhere an inner portion of the cap body 41 of a cap 40A to a side face 33b of the distal end portion 33 of the probe 3. In this case, the heat generated from the light-irradiated portion of the white plate 42 is conducted to the adhesive 43 through the air or the cap body 41 from the white plate 42.

Figure 8:
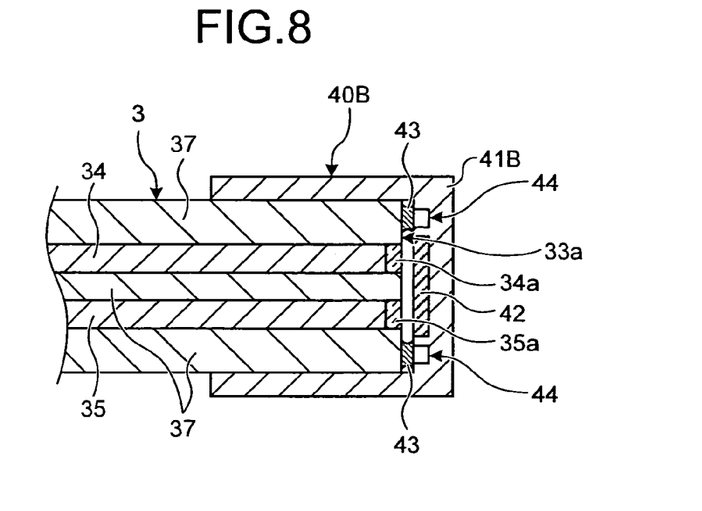
FIG. 8 is a cross-sectional view illustrating another example of the distal end portion of the probe illustrated in FIG. 1.
Figure 9:
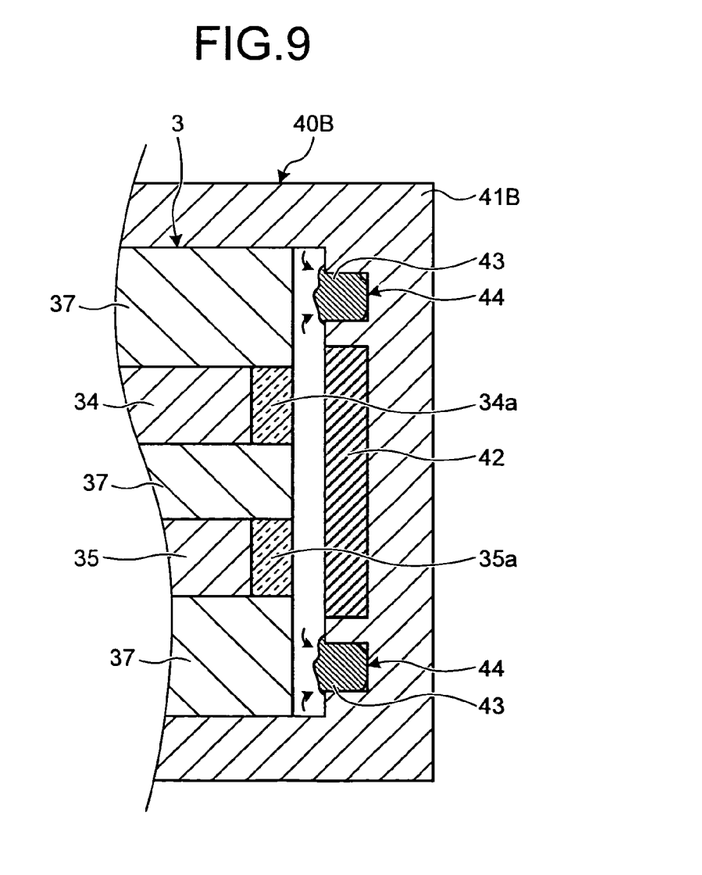
FIG. 9 is a cross-sectional view for explaining removal of the cap from the distal end portion of the probe illustrated in FIG. 8.

In addition, as illustrated with a cap 40B of FIG. 8, a concave portion 44 may be formed in the internal bottom surface of a cap body 41B facing the distal end face 33a of the probe 3, and the adhesive 43 may be provided on the surface of the concave portion 44 to block an opening of the concave portion 44. In such a configuration, when the cap 40B is separated from the distal end portion 33 of the probe 3, the adhesive 43 melted by the application of heat retreats to the concave portion 44 as indicated by an arrow in FIG. 9. As a result, it is possible to infallibly prevent the adhesive 43 from remaining on the distal end portion 33 of the probe 3 when the cap 40B is removed from the distal end portion 33 of the probe 3.

Figure 10:
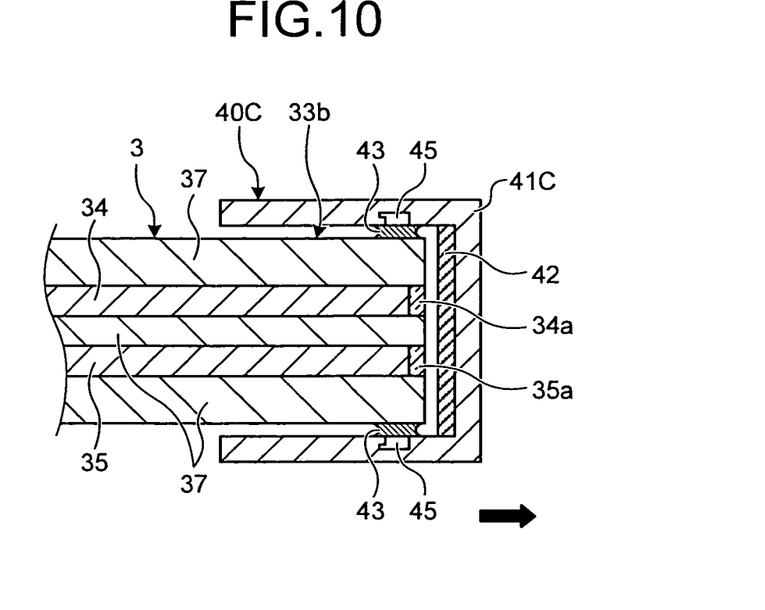
FIG. 10 is a cross-sectional view illustrating another example of the distal end portion of the probe illustrated in FIG. 1.

Like a cap 40C illustrated in FIG. 10, a concave portion 45 may be provided in an inner side face of a cap body 41C facing the side face 33b of the distal end portion 33 of the probe 3. In addition, a hollow in a direction opposite to a removal direction of the cap 40C may be provided in the side face of the concave portion 45 so that the adhesive 43 is able to easily follow toward the cap 40C upon removal of the cap 40C.

Figure 11:
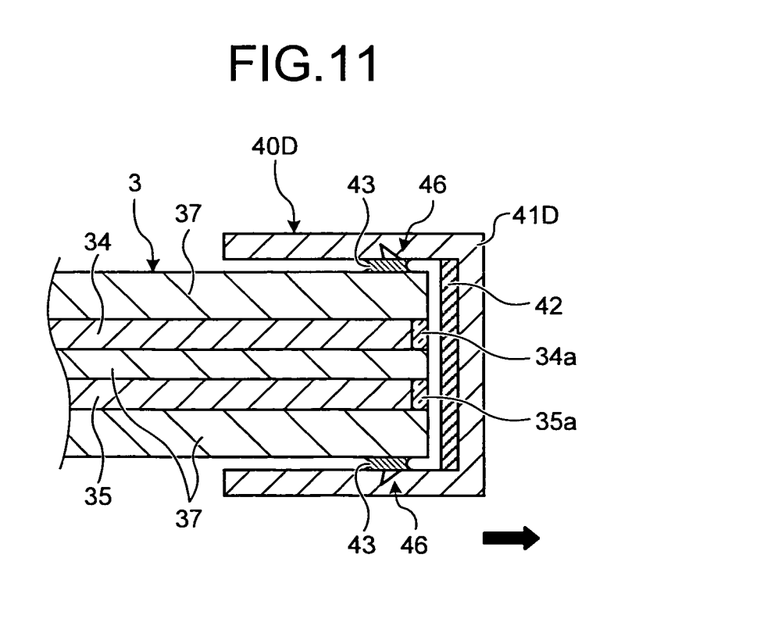
FIG. 11 is a cross-sectional view illustrating another example of the distal end portion of the probe illustrated in FIG. 1.

As in a cap 40D illustrated in FIG. 11, a concave portion 46 having a wedge shape may be provided on a side face inside a cap body 41D. This concave portion 46 is inclined toward a direction opposite to a removal direction of the cap 40D so that the adhesive 43 is able to easily follow toward the cap 40D upon removal of the cap 40D.

Second Embodiment

Figure 12:
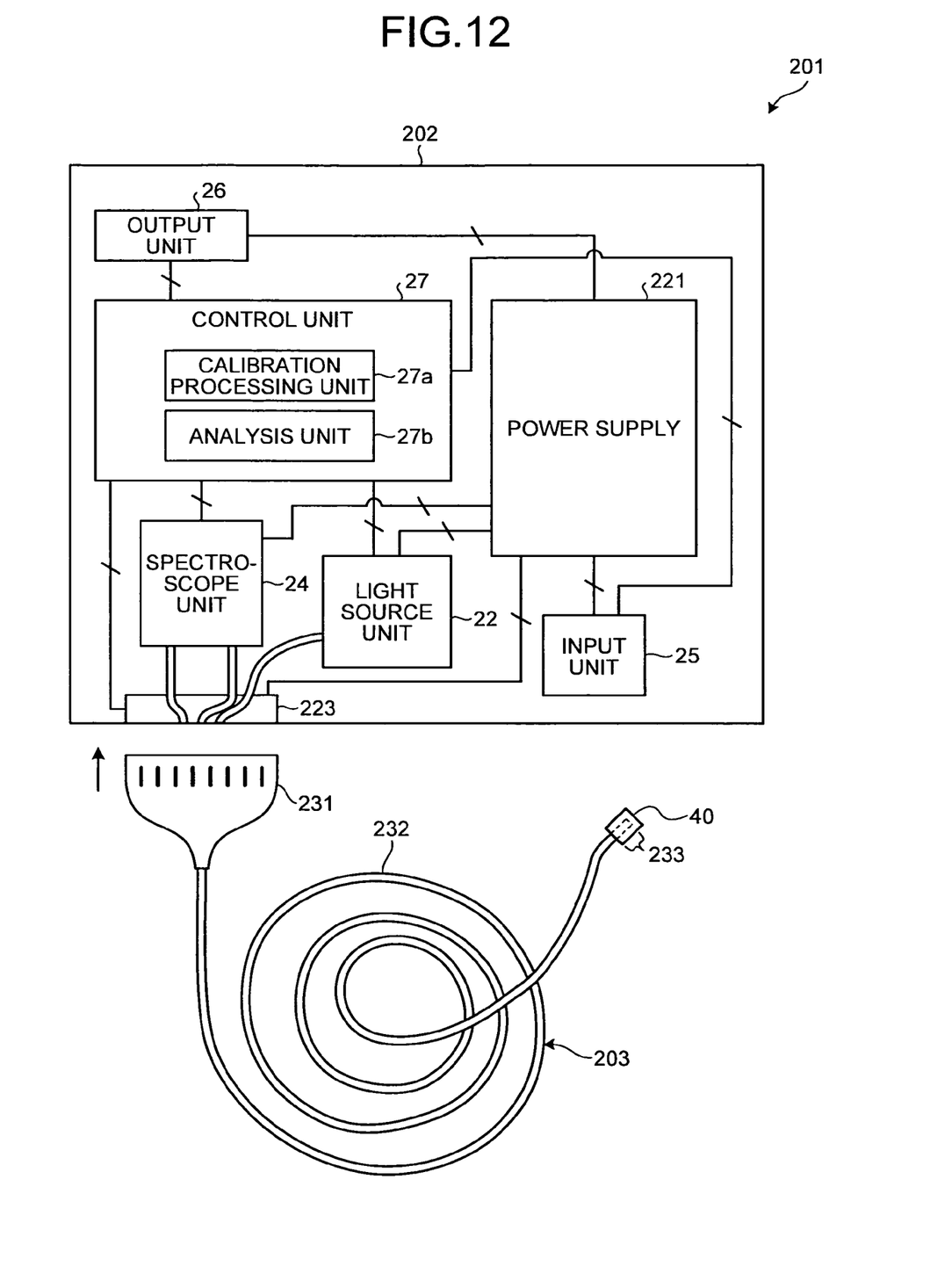
FIG. 12 is a schematic diagram illustrating a schematic configuration of an optical measurement apparatus according to a second embodiment.

Next, a second embodiment will be described. FIG. 12 is a schematic diagram illustrating a schematic configuration of the optical measurement apparatus according to the second embodiment. As illustrated in FIG. 12, an optical measurement apparatus 201 according to the second embodiment includes a detection device 202 and a probe 203.

The detection device 202 has a power supply 221 that supplies power to the probe 203 via a connector 223 in place of the power supply 21 in the detection device 2 illustrated in FIG. 1. The connector 223 has a function similar to that of the connector 23 and supplies the power supplied from the power supply 221 to the probe 203.

Similarly to the probe 3, the probe 203 includes a proximal end portion 231 detachably connected to the connector 223 of the detection device 202, a flexible portion 232 having flexibility, and a distal end portion 233 from which light supplied from a light source unit 22 is emitted and into which the scattered light from an object to be measured enters. Similarly to the probe 3, the probe 203 is provided with a cap 40 being installed, which covers the distal end portion 233.

Figure 13:
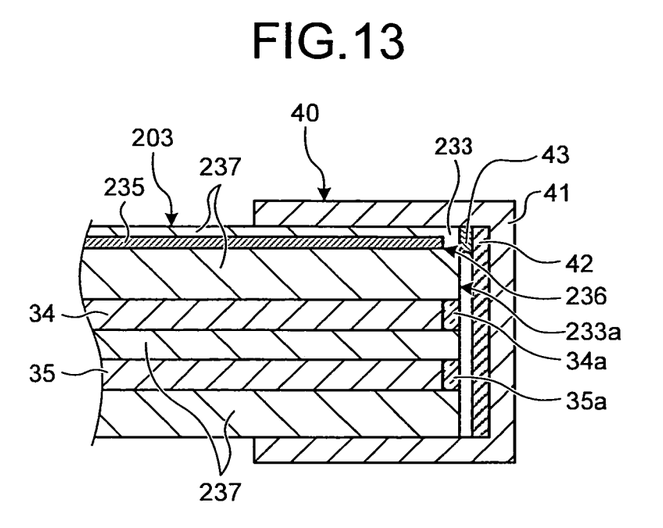
FIG. 13 is a cross-sectional view of a distal end portion of a probe illustrated in FIG. 12 cut along an axial direction of the probe.

Next, the probe 203 will be described. FIG. 13 is a cross-sectional view of the distal end portion 233 of the probe 203 illustrated in FIG. 12 cut along an axial direction of the probe 203. The probe 203 includes an irradiation fiber 34, a light-collecting fiber 35, and an electric line 235. The electric line 235 has a proximal end (not illustrated) connected to the power supply 221 via the connector 223, and a distal end 236 extending to the vicinity of a distal end face 233a of the distal end portion 233 of the probe 203.

The probe 203 is formed by covering the irradiation fiber 34, the light-collecting fiber 35, and the electric line 235 with a covering member 237 having thermal conductivity. Similarly to the first embodiment, an inner portion of the cap 40 and the distal end portion 233 of the probe 203 are adhered together by the use of an adhesive 43.

The electric line 235 generates heat at the distal end 236 by the power supplied from the power supply 221. A covering member 237 conducts the heat generated at the distal end 236 of the electric line 235 to the adhesive 43.

The adhesive 43, by adjustment of an adhesive amount, adhesive area, or the like, is melted by the heat generated at the distal end 236 of the electric line 235 based on the power supplied by the power supply 221 during an interval between start and end of a calibration process. Therefore, similarly to the first embodiment, in the second embodiment, it is possible to remove the cap 40 from the distal end portion 233 of the probe 203 after the calibration process is finished.

Figure 14:
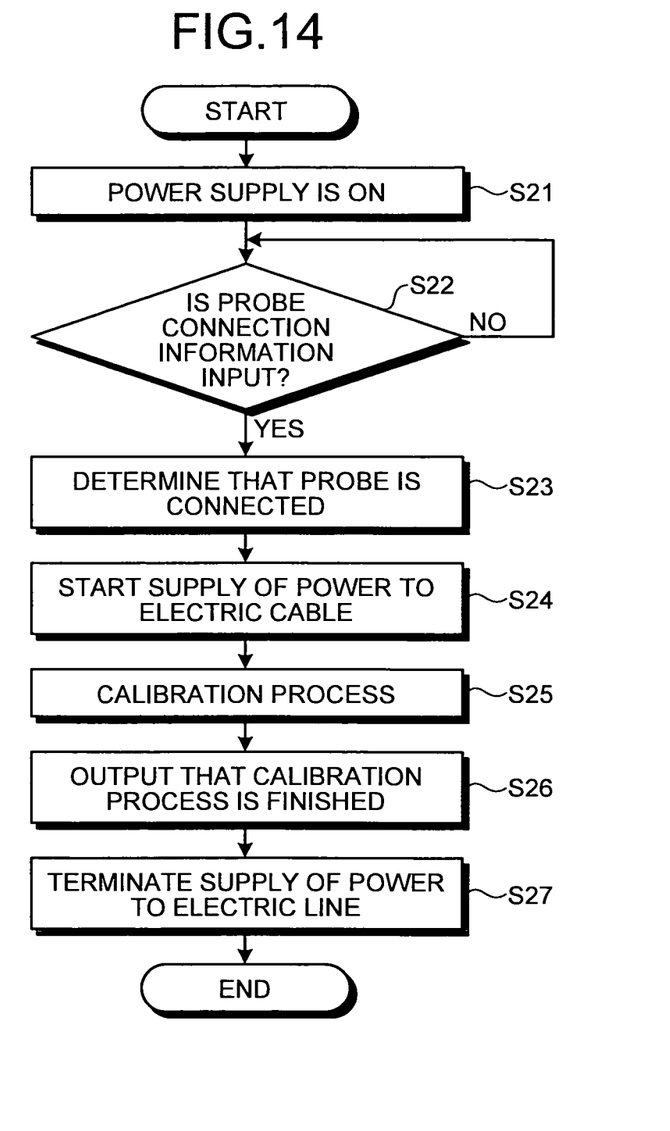
FIG. 14 is a flowchart illustrating a processing sequence until the optical measurement apparatus illustrated in FIG. 12 finishes a calibration process.

Next, a processing sequence until the optical measurement apparatus 201 finishes the calibration process will be described. FIG. 14 is a flowchart illustrating a processing sequence until the optical measurement apparatus 201 illustrated in FIG. 12 finishes the calibration process.

First, as illustrated in the flowchart of FIG. 14, similarly to steps S1 and S2 of FIG. 5, the power supply 221 is turned on (step S21), and an input determination process for probe connection information by the control unit 27 is performed (step S22). When the control unit 27 determines that the probe connection information has not been input (NO in step S22), the control unit 27 repeats the determination process of step S22 until the control unit 27 determines that the probe connection information has been input.

When the control unit 27 determines that the probe connection information has been input (YES in step S22), the control unit 27 determines that the probe 203 has been connected to the detection device 202 (step S23). Subsequently, the control unit 27 causes the power supply 221 to start supplying power to the electric line 235 (step S24). Thereafter, the calibration processing unit 27a performs the calibration process (step S25).

After the calibration process in step S25 is finished, the control unit 27 causes the output unit 26 to output that the calibration process is finished (step S26). Subsequently, the control unit 27 causes the power supply 221 to terminate the supply of power to the electric line 235 (step S27), and finishes the calibration process.

Here, the adhesive 43 that adheres the cap 40 and the distal end portion 233 of the probe 203 together is melted by the heat generated at the distal end 236 of the electric line 235 based on the power supplied by the power supply 121 during an interval between the start and end of the calibration process. Therefore, as the calibration is finished, the cap 40 becomes separable from the distal end portion 233 of the probe 203 and the cap 40 becomes removable from the distal end portion 233 of the probe 203.

In the second embodiment, by melting the adhesive 43 adhering the cap 40 to the distal end portion 233 of the probe 203 by supplying power to the electric line 235 inside the probe 203 to generate heat, the cap becomes removable for the first time after the calibration process is finished. Therefore, according to the second embodiment, similarly to the first embodiment, it is possible to infallibly perform the calibration process before measurement on an actual object to be measured, and to obtain an appropriate measurement result.

In the second embodiment, although an example in which the heat is conducted to the adhesive 43 from the electric line 235 via the covering member 237 has been described, limitation is not made thereto. If there is a gap between the cap body 41 and the covering member 237, the heat is conducted to the adhesive 43 via the air interposed between the cap body 41 and the covering member 237.

Figure 15:
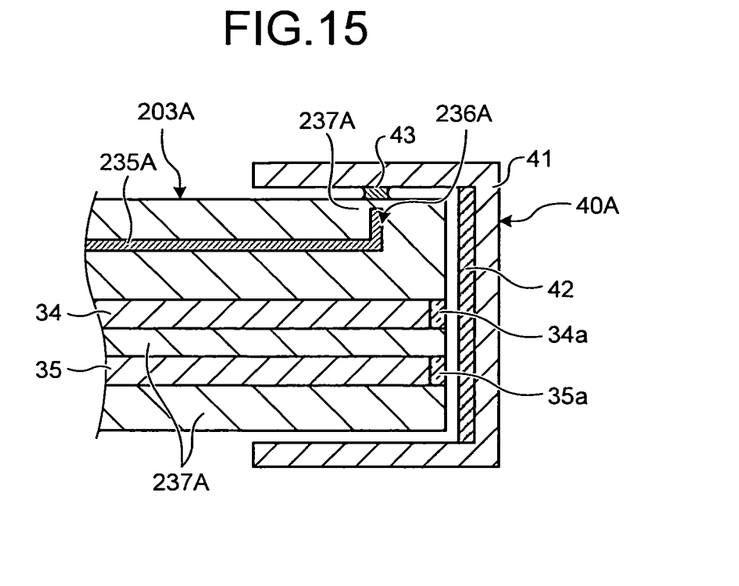
FIG. 15 is a cross-sectional view illustrating another example of a distal end portion of the probe illustrated in FIG. 12.

In addition, as illustrated in FIG. 15, when an adhesive 43 adheres an inner portion of a cap body 41 of a cap 40A to a side face 33b of a distal end portion 233 of a probe 203A, an electric line 235A may be bent such that a distal end 236A is positioned in the vicinity of an adhered portion. In this case also, heat generated at the distal end 236A of the electric line 235A is conducted to the adhesive 43 through a covering member 237A. In the second embodiment, the distal end portion 233 of the probe 203 may be covered by any one of the caps 40B to 40D described in the first embodiment.

Further, although description has been made for the optical measurement apparatuses that detect scattered light in the first and second embodiments, the present invention may be applied to an optical measurement apparatus that detects reflected light from an object to be measured or an optical measurement apparatus that detect both reflected light and scattered light.

Furthermore, although description has been made for examples in which the white plate 42 is used as a standard object for calibration measurement in the first and second embodiments, the standard object is not limited to the white plate as long as the standard object has stable reflection characteristics.

Additional effects and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A probe detachably connected to an optical measurement apparatus, comprising:
    a fiber that emits, from a distal end thereof, light supplied from a proximal end thereof by the optical measurement apparatus, and outputs, from the proximal end to the optical measurement apparatus, reflected light and/or scattered light from an object to be measured, the reflected light and/or scattered light entering from the distal end;
    a covering member that covers a side face of the fiber;
    a cap that covers a distal end of the probe, a standard object being provided on a surface of the cap facing the distal end of the fiber, the standard object being configured for a calibration measurement by light emitted from the distal end of the fiber;
    an adhesive member that adheres the cap to the distal end of the probe and is made of an adhesive having an adhesive strength with respect to the covering member, the adhesive strength decreasing by application of heat;
    a heat-generating portion that generates heat to be applied to the adhesive member; and
    a thermal conduction portion that conducts, to the covering member, the heat that decreases the adhesive strength of the adhesive material with respect to the covering member, wherein
    the cap including the standard object becomes removable from the probe after the calibration measurement due to melting of the adhesive,
    the adhesive strength of the adhesive with respect to the covering member decreases to be lower than an adhesive strength of the adhesive with respect to the cap when the heat generated during the calibration measurement is applied to the adhesive member and the adhesive is melted,
    the thermal conduction portion conducts, to the adhesive member, the heat generated by the heat-generating portion, and
    once the cap is removed from the probe, the optical measurement apparatus detects characteristics of the object to be measured.

2. The probe according to claim 1, wherein the heat-generating portion generates the heat based on light irradiated by the fiber.

3. The probe according to claim 1, wherein the heat-generating portion has an electric line which has a distal end extending to the vicinity of the distal end of the probe and to which power is supplied from outside.

4. The probe according to claim 1, wherein the adhesive member has an adhesive strength with respect to the cap that becomes stronger than the adhesive strength with respect to the covering member when heat is applied to the adhesive member.

5. The probe according to claim 1, wherein the adhesive member is melted when heat is applied.

6. The probe according to claim 1, wherein the cap is provided with a concave portion, and the adhesive member is provided on a surface of the concave portion.

7. The probe according to claim 1, wherein the adhesive member adheres the cap to a distal end face of the distal end of the probe.

8. The probe according to claim 1, wherein the adhesive member adheres the cap to a side face of the distal end of the probe.

9. The probe according to claim 1, wherein the adhesive member is a thermoplastic adhesive.

10. The probe according to claim 1, wherein
    the adhesive member adheres to the cap and does not remain on the covering member after the cap is removed from the probe.

11. An optical measurement apparatus, comprising:
    a probe including:
        a fiber that emits, from a distal end thereof, light supplied from a proximal end thereof by the optical measurement apparatus, and outputs, from the proximal end to the optical measurement apparatus, reflected light and/or scattered light from an object to be measured, the reflected light and/or scattered light entering from the distal end;
        a covering member that covers a side face of the fiber;
        a cap that covers a distal end of the probe, a standard object being provided on a surface of the cap facing the distal end of the fiber, the standard object being configured for a calibration measurement by light emitted from the distal end of the fiber;
        an adhesive member that adheres the cap to the distal end of the probe and is made of an adhesive having an adhesive strength with respect to the covering member, the adhesive strength decreasing by application of heat;
        a heat-generating portion that generates heat to be applied to the adhesive member; and
        a thermal conduction portion that conducts, to the covering member, the heat that decreases the adhesive strength of the adhesive material with respect to the covering member;
    a connector to which a proximal end of the probe is detachably connected;
    a light source that supplies light to the probe via the connector;
    a light-receiving unit that receives via the connector light output from the probe;
    a measurement unit that measures a characteristic of the object to be measured based on a result of the light-reception by the light-receiving unit; and
    a calibration processing unit that performs a calibration process of the optical measurement apparatus and the probe, wherein
    the cap including the standard object becomes removable from the probe after the calibration measurement due to melting of the adhesive,
    the adhesive strength of the adhesive with respect to the covering member decreases to be lower than an adhesive strength of the adhesive with respect to the cap when the heat generated during the calibration measurement is a lied to the adhesive member and the adhesive is melted,
    the thermal conduction portion conducts, to the adhesive member, the heat generated by the heat-generating portion, and
    once the cap is removed from the probe, the optical measurement apparatus detects characteristics of the object to be measured.

12. The optical measurement apparatus according to claim 11, wherein the heat-generating portion generates heat based on light irradiated by the fiber.

13. The optical measurement apparatus according to claim 11, wherein the heat-generating portion has an electric line having a distal end extending to the vicinity of the distal end of the probe and power is supplied from outside.

14. The optical measurement apparatus according to claim 11, further comprising an output unit that outputs information indicating that the calibration process is finished when the calibration process is finished.

15. The optical measurement apparatus according to claim 11, further comprising an endoscope to be inserted into a body, wherein the probe is inserted into the body by being inserted from a predetermined channel insertion hole positioned at an out-of-body portion of the endoscope and protruding from an opening that is an aperture of a distal end of the endoscope and that is connected to a predetermined channel, and an outer diameter of the cap is larger than a diameter of the channel insertion hole.

16. The optical measurement apparatus according to claim 11, wherein when heat is applied, the adhesive member has an adhesive strength to the cap stronger than an adhesive strength to the covering member.

17. The optical measurement apparatus according to claim 11, wherein the adhesive member is melted when heat is applied.

18. The optical measurement apparatus according to claim 11, wherein the cap is provided with a concave portion, and the adhesive member is provided on a surface of the concave portion.

19. The optical measurement apparatus according to claim 11, wherein the adhesive member adheres the cap to a distal end face of the distal end of the probe.

20. The optical measurement apparatus according to claim 11, wherein the adhesive member adheres the cap to a side face of the distal end of the probe.

21. The optical measurement apparatus according to claim 11, wherein the adhesive member is a thermoplastic adhesive.

22. The optical measurement apparatus according to claim 11, wherein the light source is an incoherent light source.

* * * * *